United States Patent [19]

De Munck et al.

[11] Patent Number: 5,324,420
[45] Date of Patent: Jun. 28, 1994

[54] SULFUR REMOVAL FROM HYDROCARBONS WITH NICKEL CONTAINING CATALYST

[75] Inventors: Nicolaas A. De Munck, Barendrecht, Netherlands; Arie Van Vliet, Bondues, France

[73] Assignee: Exxon Chemical Patents Inc., Linden, N.J.

[21] Appl. No.: 962,221

[22] PCT Filed: Jul. 25, 1991

[86] PCT No.: PCT/EP91/01416

§ 371 Date: Apr. 16, 1993

§ 102(e) Date: Apr. 16, 1993

[87] PCT Pub. No.: WO92/02478

PCT Pub. Date: Feb. 20, 1992

[30] Foreign Application Priority Data

Jul. 27, 1990 [EP] European Pat. Off. ........ 90308247.7
Jul. 27, 1990 [GB] United Kingdom ................. 9016574

[51] Int. Cl.$^5$ ................. C10G 11/02; C10G 25/05
[52] U.S. Cl. ................. 208/124; 208/91; 208/58; 208/64
[58] Field of Search ............ 208/111, 89, 91, 124, 208/58, 64; 502/33, 515; 568/454, 881, 882

[56] References Cited

U.S. PATENT DOCUMENTS

| | | | |
|---|---|---|---|
| 4,634,515 | 1/1987 | Bailey et al. | 208/91 |
| 5,030,774 | 7/1991 | Oswald et al. | 568/882 |
| 5,082,977 | 1/1992 | Chaung | 568/454 |

*Primary Examiner*—R. Bruce Breneman
*Assistant Examiner*—Bekir L. Yildirim
*Attorney, Agent, or Firm*—J. J. Mahon

[57] ABSTRACT

Treatment of sulphur bearing hydrocarbons, especially olefin feedstocks to the oxo process, with a nickel-containing catalyst, especially spent hydrogenation catalyst, which may be amine treated.

8 Claims, No Drawings

SULFUR REMOVAL FROM HYDROCARBONS WITH NICKEL CONTAINING CATALYST

This invention relates to the treatment of sulphur-bearing hydrocarbon feedstocks, and especially to the removal of sulphur from the feedstock. In particular, the invention relates to treatment of olefin feedstocks, especially those to be hydroformylated by the oxo process to produce alcohols used in esterification.

Olefins, in hydroformylation feedstocks for example, frequently have sulphur-containing impurities. Thiols, thiophenes, hydrogen sulphide, and other sulphur-containing compounds may make the feed unacceptable because of the tendency for the sulphur rapidly to poison the catalyst used, either in the hydroformylation or, especially, if the resulting aldehyde is to be reduced over a catalyst, e.g. copper chromite, nickel or cobalt, either supported or unsupported, to an alcohol. In particular, the selectivity and activity of a copper chromite catalyst are both adversely affected by sulphur, and cobalt or nickel catalysts suffer a loss in activity.

That such feedstocks may be desulphurized has been disclosed, without details of the procedure, in a brochure entitled "Oxo-alcohols and Plasticizers" published by Exxon Chemical Holland Inc.

It has been proposed, in British Specification No. 1142339, to remove carbon oxysulphide from $C_3$ feedstocks by their passage in the liquid phase over an oxide of cadmium, zinc, nickel or cobalt on a carrier.

In U.S. Pat. No. 4,592,829, it is proposed to hydrofine a reformer feedstock containing a preponderance of aromatics and lesser amounts of paraffins and olefins, and to complete the desulphurization of the hydrofined feedstock by passing it over a supported nickel/iron catalyst. In U.S. Pat. No. 4,634,515 desulphurization of a hydrofined naphtha feedstock is completed over a nickel catalyst of greater than normal average crystallite size, having at least 50% of the nickel in the reduced state. Desulphurization of aromatic hydrocarbon feedstocks and of feedstocks composed of paraffinic and unsaturated heavier hydrocarbons over the nickel-containing catalyst designated "Girdler G-134 A RS" is advocated in a brochure entitled "Katalysatoren der SÜD-Chemie AG" published by that company.

The present invention provides a process for the manufacture of an aldehyde, and optionally of an alcohol or an acid, by hydroformylation of an olefin-containing feedstock and optional subsequent hydrogenation using a catalyst, e.g. copper chromite, nickel or cobalt, either supported or unsupported, susceptible to sulphur poisoning, wherein a sulphur-bearing olefin-containing feedstock is contacted under substantially non-hydrogenating conditions with a nickel-containing catalyst, whereby the sulphur content of the feedstock is lowered, the resulting reduced-sulphur feedstock is hydroformylated, and optionally the resulting aldehyde reduced to form an alcohol or oxidized to form an acid.

The invention also provides the use of a nickel-containing catalyst in desulphurization of an olefin feedstock to a hydroformylation process, especially to a hydroformylation process followed by reduction to an alcohol or oxidation to an acid.

The olefin feedstock may contain $C_3$ to $C_{18}$, advantageously $C_4$ to $C_{12}$, more advantageously $C_4$ to $C_6$, olefins, and preferably comprises pentene or hexene.

The feedstock is advantageously contacted with the nickel-containing catalyst at a temperature and under a pressure such that the feedstock is liquid. Although precise conditions depend on the feedstock, for hexene and similar olefins a pressure within the range of 20 to 40 bar and a temperature within the range of from 150° to 200° C., advantageously 165° to 190° C., are generally preferred, the precise temperature range depending also on the catalyst. Temperatures above the range indicated above are to be avoided if formation of oligomeric compounds is to be avoided; at lower temperatures the effectiveness of sulphur removal is reduced. Within the effective range, optimum temperature will depend also on the catalyst and, during operation, its sulphur loading, higher loadings corresponding to higher temperatures. It is important that the conditions be such as substantially not to hydrogenate the olefin, and preferably the feedstock is completely hydrogen free.

As metallic nickel-containing catalyst, there may be mentioned especially a supported metal catalyst (although unsupported metal catalysts are also possible), especially a catalyst supported on a refractory material, e.g. an inorganic oxide, for example silica, alumina, clay, diatomaceous earth, (e.g. Kieselguhr), active carbon, zeolite, magnesia, or mixtures of any two or more such materials, especially a silica/alumina support.

A preferred support is one having a particle size of from 0.5 to 3.0 mm, surface area of at least 50 m$^2$/g, a bulk density of from 0.3 to 1.5 g/ml, an average pore volume of from 0.1 to 1.1 ml/g and an average pore diameter of about 3 to 500 nm.

The catalyst is advantageously a reduced nickel catalyst. In particular, it is preferred that the catalyst should be substantially fully reduced, and advantageously at least 80%, preferably at least 90%, of the nickel present should be in the metallic state at the beginning of desulphurization. It is believed that during desulphurization a sulphide of nickel, or a mixture of sulphides of nickel, is formed. Accordingly, at any time during the desulphurization reaction, advantageously at most 20%, and preferably at most 10%, of the nickel present is in the form of an oxide.

Advantageously, the catalyst has a nickel content of at least 35%, preferably from 45 to 65%, by weight, based on the total weight of catalyst, including support if present. It is within the scope of the invention to employ a catalyst including metals other than nickel, for example a nickel-zinc catalyst.

As examples of suitable catalysts there may be mentioned Girdler G-49 RS, or Girdler G-134 RS; Engelhard/Harshaw Ni-5124T, Ni-5126T, Ni-5256E, or Ni-3288E; or Hoechst Ni55/5TS.

The rate at which the olefin may be passed over the catalyst will vary with the olefin, the catalyst, the maximum proportion of sulphur tolerable in the treated feed, and the level of sulphur already in the catalyst. Advantageously, however, a space velocity in the range of 0.5 to 2.5 v.v.hr$^{-1}$, and preferably 1.4 to 1.6 v.v.hr$^{-1}$, is employed.

As indicated above, the reaction is carried out in substantially non-hydrogenating conditions. Advantageously, the reaction is carried out under completely non-hydrogenating conditions, with substantially complete exclusion of hydrogen. The presence of oxygen or oxidizing atmospheres generally is also preferably avoided.

It has surprisingly been found that spent nickel catalyst from other operations carried out on virtually sulphur-free feedstock, e.g. hydrogenation or hydrofining, may be used as desulphurization catalyst. Such catalysts contain carbon, or carbon compounds, at a level, measured as carbon, of up to 20, especially from 5 to 20, and more specifically 8 to 15, percent by weight, based on the total weight of catalyst, including support if present. The present invention accordingly also provides a process for desulphurization of a hydrocarbon feed using a spent hydrofining nickel-containing catalyst. The invention still further provides the use of a spent hydrofining nickel-containing catalyst for desulphurizing a hydrocarbon feed. Especially the invention provides such a process, and a use of such a catalyst, in which the feedstock is an olefin feedstock, and preferably a feedstock to a hydroformylation (oxo) process.

In some circumstances it is desirable to effect desulphurization with the minimum possible change in the hydrocarbon make-up of the feedstock. This is the case, for example, when the product of the hydroformylation (oxo) process is to be reduced, and the resulting alcohol is to be esterified to form a plasticizer. If oligomerization of the feedstock olefins takes place, the resulting dimeric and trimeric olefins may not be completely hydroformylated, and the high molecular weight olefins contaminate the alcohol and ester, lessening its purity and causing the alcohol and plasticizer to develop an undesirable colour. The techniques of the present invention have been found to significantly reduce these problems.

It has unexpectedly been found that spent catalyst effects less change to the feedstock hydrocarbon make-up than the corresponding fresh catalyst.

A spent catalyst may be a catalyst that has expended its useful life as a hydrogenation catalyst. Typically in use as a hydrogenation catalyst a fresh nickel catalyst is loaded into a reactor in an inert (nitrogen) atmosphere. After catalyst loading the catalyst temperature is increased to 50°–150° C., while flowing nitrogen. After having reached 50° to 150° C. depending on the type of catalyst, hydrogen is admixed to the nitrogen stream initially at low volume % (5) later on steadily increased to 100%. After completion of the activation process the catalyst is subjected to the hydrocarbon feed to be hydrogenated. Alternatively the catalyst can be activated with a saturated hydrocarbon stream in the presence of nitrogen following the above method.

At the end of its useful life as a hydrogenation catalyst the feed to reactor is ceased and the liquids in the reactor are purged with nitrogen. After purging the reactor contents and cooling down the reactor can be opened for unloading. The catalyst is put under nitrogen into drums or containers, subsequently sieved to remove fines and transferred into the desulfurization reactor. We have found that this catalyst may now be used for desulfurization without any additional activation. An alternative unloading method is to steam out the catalyst before unloading into drums.

The spent catalyst is the original fresh catalyst plus contained carbon and sulfur, which are picked up during the hydrogenation process.

It has also surprisingly been found that, whether the catalyst is fresh or spent, when the catalyst is supported on a support containing calcium and/or silicon, less change is effected to the make-up if (a) the content of silicon is less than 4%, based on the total weight of catalyst and support; (b) if the content of calcium is at least 1%, advantageously at least 1.5%, based on the total weight of catalyst and support and, especially, (c) if the weight ratio of silicon:calcium is less than 4:1 and preferably less than 2:1. The use of a support substantially free of silicon is also advantageous.

It has unexpectedly been found that when a spent catalyst is employed, it is possible to use it until its sulphur content has reached a higher level than with the corresponding fresh catalyst while reducing the sulphur content of the feedstock to the same level. This is because, under given conditions, the spent catalyst causes less change in the hydrocarbon make-up of the feedstock.

Since, in operation, it is necessary as the catalyst sulphur level increases gradually to increase the temperature to reduce the sulphur content of the treated feedstock to a given level, and oligomerization takes place more readily at higher temperatures, it is possible to run the operation at a higher temperature with the spent catalyst than with the corresponding fresh catalyst and retain the same hydrocarbon make-up of the treated feedstock.

As a result, it is possible to treat a greater quantity of feedstock using a spent catalyst than using a fresh catalyst, while still yielding a treated feedstock of acceptable quality.

In a further preferred embodiment of the invention the nickel-containing catalyst is aminated which can inhibit undesirable dimersation of the olefin during desulphurisation.

The catalyst may be aminated by direct treatment with an amine, conveniently under temperature and pressure conditions similar to those used for desulphurization. The amine may be admixed with or dissolved in an olefin at a concentration of, for example 0.1 to 10% by weight, advantageously 0.5 to 2%, and preferably about 1% and the amine-containing olefin passed through the catalyst for, for example, from 1 to 40 hours, advantageously 10 to 30 hours, and preferably for from 20 to 28 hours. Alternatively, the catalyst may be treated with the amine, if desired in admixture with or in solution in the alcohol which results from hydroformylation and hydrogenation of the olefin under consideration, by immersing the catalyst in the amine at ambient temperature for, for example, 24 hours.

As amines there may be mentioned primary, secondary or tertiary amines, aliphatic and cycloaliphatic amines being preferred. Advantageously, the amine is a monoamine; the molecule may contain other substituents or functional groups, e.g. a hydroxy group, provided that the basicity of the molecule is not adversely affected. Strongly basic amines, i.e. those with low $pK_b$ values, e.g. less than 4.5, but preferably less than 3.5, are preferred. Advantageously, the amine has a boiling point at somewhat above that of the olefin being treated, under the conditions of olefin desulphurization being used.

Among suitable amines there may be mentioned, for example, methylamine, trimethylamine, ethylamine, dipropylamine, butylamine, tributylamine, ethanolamine and diethanolamine. Among amines with low $pK_b$ values, and appropriate boiling ranges, and therefore preferred, there may be mentioned dimethylamine, dieetylamine, trietylamine, dibutylamine, piperidine and pyrrolidine.

In the embodiments of this invention in which hydroformylation takes place, the reaction conditions of that stage of the process are per se conventional, as are those of any subsequent reaction, e.g. oxidation, hydrogenation, and hydrofining and will not be given here. It has been found, however, that by the desulphurization of the feed according to the present invention catalyst life, especially in the hydrogenation stage, is enhanced to a surprising extent and the purity of the product is surprisingly improved.

The following Examples illustrate the invention:

EXAMPLE 1

A tubular reactor of 13.7 mm diameter, 207 mm length, was loaded with 29.0 g of fresh Engelhard/Harshaw Ni-5124T catalyst (Analysis: 61% Ni; 6% Al; 4% Si; 0.4% Ca; 0.1% Fe). After a nitrogen purge at ambient temperature, the reactor was immersed in a fluidized sandbath to maintain it at a constant temperature within a desired, in this example 165° C. to 175° C., operating range. An olefinic (primarily a mixture of different hexene isomers obtained by dimerizing propylene over an acidic catalyst) feed-stock having the analysis shown in Table 1 was passed through the reactor.

TABLE 1

| | |
|---|---|
| Carbon number distribution | See Table 3 |
| Paraffin content | 9.8% |
| Sulphur | 120 ppm |
| Chlorine | 2 ppm |
| S.G. (20/20° C.) | 0.693 |
| Maleic Anhydride Value | 0.25 mg/g |
| ASTM D1078 Distillation | see Table 4 |

The catalyst was on stream for a total of 473 hours; the details of reaction conditions and sulphur loadings in the treated feedstock and catalyst at various intervals are shown in Table 2.

The resulting sulphur level in the treated feedstock in Run 1 indicated that initially too high a space velocity (1.90 v.v.hr$^{-1}$) was being used for the conditions possibly in combination with the reactor temperature not having reached the temperature indicated by the sandbath thermometer. Run No. 2, at a lower space velocity (1.50), showed an extremely high rate of reduction in residual sulphur; the reduction was improved still further by an increase in temperature from 165° C. to 170° C. An increase to 175° C. again reduced sulphur to below 1 ppm after a sulphur breakthrough occurred at 378 hours (4.2% by weight sulphur on catalyst).

TABLE 2

| RUN NUMBER 1- | TOTAL TIME ON STREAM hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 19 | 165 | 1.90 | 120 | 64 | 0.13 |
| 2 | 43 | 165 | 1.50 | 120 | 3 | 0.40 |
| 3 | 114 | 170 | 1.48 | 120 | 1 | 1.21 |
| 4 | 142 | 170 | 1.49 | 120 | <1 | 1.53 |
| 5 | 162 | 170 | 1.48 | 120 | <1 | 1.76 |
| 6 | 186 | 170 | 1.47 | 120 | <1 | 2.03 |
| 7 | 210 | 170 | 1.47 | 120 | <1 | 2.31 |
| 8 | 281 | 170 | 1.45 | 120 | <1 | 3.10 |
| 9 | 330 | 170 | 1.45 | 120 | <1 | 3.65 |
| 10 | 378 | 170 | 1.44 | 120 | 1 | 4.18 |
| 11 | 449 | 175 | 1.47 | 120 | <1 | 4.99 |
| 12 | 473 | 175 | 2.17 | 120 | 2 | 5.39 |

The carbon number distributions and wt % paraffins in Table 3 below show that the hydrocarbon make-up of the feedstock was substantially unaffected by the desulphurization process although the dimer formation rate increased when the temperature was raised to 175° C., results confirmed by the distillation pattern shown in Table 4.

TABLE 3
CARBON NUMBER DISTRIBUTIONS FOR HEXENE FEED AND DESULPHURIZED PRODUCTS

| CARBON NUMBER | FEED | RUN 1-3 | 1-8 | 1-9 | 1-10 | 1-11 |
|---|---|---|---|---|---|---|
| wt % ≤ C$_5$ | 0.12 | 0.18 | 0.04 | 0.03 | 0.04 | 0.04 |
| C$_6$ | 83.95 | 83.40 | 83.83 | 85.73 | 85.33 | 83.23 |
| C$_7$ | 15.23 | 15.57 | 15.22 | 13.40 | 13.76 | 15.60 |
| C$_8$ | — | — | — | — | — | — |
| C$_9$ | 0.02 | 0.02 | 0.01 | 0.01 | 0.01 | 0.02 |
| C$_{10}$ | 0.14 | 0.14 | 0.14 | 0.13 | 0.14 | 0.15 |
| C$_{11}$ | 0.18 | 0.17 | 0.17 | 0.15 | 0.16 | 0.17 |
| C$_{12}$ | 0.37 | 0.43 | 0.50 | 0.47 | 0.48 | 0.66 |
| C$_{13}$ | 0.07 | 0.08 | 0.09 | 0.08 | 0.08 | 0.11 |
| C$_{14}$ | 0.01 | 0.01 | — | — | — | — |
| wt % paraffin | 9.85 | 9.98 | 9.95 | 9.82 | 9.86 | 9.89 |
| Temperature Reactor ° | — | 170 | 170 | 170 | 170 | 175 |
| VVH hr$^{-1}$ | — | 1.48 | 1.45 | 1.45 | 1.44 | 1.47 |

TABLE 4
ASTM DISTILLATION (D-1078) FOR HEXENE FEED AND PRODUCTS

| ASTM DISTILLATION, °C. | FEED | RUN 1-3 | 1-8 | 1-9 | 1-10 | 1-11 |
|---|---|---|---|---|---|---|
| IBP | 66.4 | 65.7 | 65.9 | 66.0 | 66.1 | 66.0 |
| 25% | 67.8 | 67.5 | 67.6 | 67.7 | 67.6 | 67.5 |
| 50% | 68.4 | 68.2 | 68.3 | 68.3 | 68.2 | 68.2 |
| 75% | 69.4 | 69.3 | 69.3 | 69.3 | 69.4 | 69.3 |
| 95% | 72.8 | 73.5 | 73.1 | 73.0 | 73.6 | 72.7 |
| DP | 73.8 | 74.5 | 74.5 | 74.5 | 74.5 | 74.9 |

EXAMPLE 2

The procedure of Example 1 was repeated, except that the hydrofinishing catalyst was spent Girdler G-49 RS (analysis of fresh catalyst: 46% Ni; 9% Si; 0.6% Al; 0.3% Ca; 0.2% Fe). The sulphur content of the feed was 180 ppm, the paraffin content 21.6%, chlorine level <1 ppm, S.G. (15/15° C.) 0.689, and maleic anhydride value 1.28 mg/g. The catalyst as installed in the reactor had a carbon loading of 14.35%, but this did not adversely affect its ability to desulphurize the feedstock. Results are shown in Tables 5 and 6.

TABLE 5

| RUN NUMBER 2- | TOTAL TIME ON STREAM hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 24 | 170 | 1.83 | 180 | 1 | 0.45 |
| 2 | 48 | 170 | 1.63 | 180 | 5 | 0.84 |
| 3 | 71 | 167 | 1.74 | 180 | 10 | 1.23 |
| 4 | 139 | 175 | 1.69 | 180 | 11 | 2.33 |
| 5 | 187 | 175 | 1.69 | 180 | 10 | 3.12 |
| 6 | 239 | 180 | 1.75 | 180 | 9 | 4.00 |
| 7 | 305 | 185 | 1.77 | 180 | 8 | 5.14 |

TABLE 6
CARBON NUMBER DISTRIBUTION FOR HEXENE FEED AND PRODUCTS

| CARBON NUMBER | FEED | RUN 2-5 | RUN 2-6 | RUN 2-7 |
|---|---|---|---|---|
| wt % ≤ C$_5$ | 0.3 | 0.3 | 0.4 | 0.3 |
| C$_6$ | 87.4 | 85.7 | 85.4 | 84.9 |
| C$_7$ | 11.5 | 12.2 | 12.1 | 12.3 |
| C$_8$ | — | — | — | — |
| C$_9$ | — | — | — | — |
| C$_{10}$ | 0.1 | 0.1 | 0.1 | 0.1 |
| C$_{11}$ | 0.3 | 0.3 | 0.2 | 0.3 |
| C$_{12}$ | 0.3 | 1.3 | 1.6 | 1.9 |

TABLE 6-continued

CARBON NUMBER DISTRIBUTION FOR HEXENE FEED AND PRODUCTS

| CARBON NUMBER | FEED | RUN 2-5 | RUN 2-6 | RUN 2-7 |
|---|---|---|---|---|
| $C_{13}$ | 0.1 | 0.1 | 0.2 | 0.2 |
| $C_{14}$ | — | — | — | — |
| Temperature Reactor °C. | — | 175 | 180 | 185 |
| VVH hr$^{-1}$ | — | 1.69 | 1.75 | 1.77 |
| wt % sulfur | — | 3.1 | 4.0 | 5.1 |

EXAMPLE 3

The procedure of Example 2 was followed, but using fresh Girdler Catalyst G134 ARS (analysis: 48% Ni; 6.8% Si; 6.8% Al; 0.3% Ca; 0.2% Fe). As Table 7 shows, at 170° C., desulphurization was poor, but an increase in temperature to 180° C. gave improved results. It is possible that there is an induction period with this catalyst, during which the surface oxide layer on the fresh material is converted to nickel sulphide. Table 8 shows the analysis of the treated feedstock and sulphur levels in the catalyst.

TABLE 7

| RUN NUMBER 3- | TOTAL TIME ON STREAM hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 24 | 170 | 1.44 | 180 | 170 | 0.03 |
| 2 | 48 | 170 | 1.44 | 180 | 170 | 0.07 |
| 3 | 71 | 170 | 1.39 | 180 | 170 | 0.10 |
| 4 | 140 | 175 | 1.41 | 180 | 130 | 0.59 |
| 5 | 164 | 180 | 1.39 | 180 | 35 | 1.06 |
| 6 | 188 | 180 | 1.37 | 180 | 8 | 1.61 |
| 7 | 212 | 180 | 1.36 | 180 | 3 | 2.18 |
| 8 | 237 | 185 | 1.41 | 180 | 1 | 2.29 |
| 9 | 308 | 185 | 1.43 | 180 | 1 | 4.57 |

TABLE 8

CARBON NUMBER DISTRIBUTION FOR HEXENE FEED AND PRODUCTS

| CARBON NUMBER | FEED | RUN 3-6 | RUN 3-7 | RUN 3-8 | RUN 3-9 |
|---|---|---|---|---|---|
| wt % ≤ $C_5$ | 0.3 | 0.7 | 0.5 | 0.6 | 0.5 |
| $C_6$ | 87.4 | 84.6 | 84.4 | 83.2 | 81.4 |
| $C_7$ | 11.5 | 12.2 | 12.0 | 12.0 | 12.1 |
| $C_8$ | — | — | — | — | — |
| $C_9$ | — | — | — | — | — |
| $C_{10}$ | 0.1 | 0.1 | 0.1 | 0.1 | 0.1 |
| $C_{11}$ | 0.3 | 0.4 | 0.4 | 0.4 | 0.4 |
| $C_{12}$ | 0.3 | 1.8 | 2.3 | 3.4 | 4.9 |
| $C_{13}$ | 0.1 | 0.2 | 0.2 | 0.3 | 0.5 |
| $C_{14}$ | — | — | — | — | — |
| Temperature Reactor °C. | — | 180 | 180 | 185 | 185 |
| VVH hr$^{-1}$ | — | 1.37 | 1.36 | 1.41 | 1.43 |
| wt % sulfur | — | 1.61 | 2.18 | 2.79 | 4.57 |

EXAMPLE 4

Following the procedure of Example 1, fresh Engelhard/Harshaw Ni-3288 catalyst is charged to the reactor. The catalyst contains 60% nickel, 4% aluminum, 3.5% silicon, 1.8% calcium, and 0.2% iron. A hexene-based sulphur bearing olefin feed was treated. Details are shown in Tables 9 to 11.

TABLE 9

| RUN NUMBER 4- | TOTAL TIME ON STREAM hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 49 | 170 | 1.32 | 120 | 4 | 0.65 |
| 2 | 97 | 170 | 1.32 | 120 | <1 | 1.32 |
| 3 | 192 | 170 | 0.99 | 120 | <1 | 2.31 |
| 4 | 264 | 170 | 1.43 | 120 | <1 | 3.40 |
| 5 | 340 | 170 | 1.49 | 120 | 15 | 4.45 |
| 6 | 409 | 170 | 1.43 | 120 | 32 | 5.22 |
| 7 | 432 | 175 | 1.46 | 120 | 20 | 5.51 |
| 8 | 504 | 175 | 1.47 | 120 | 25 | 6.40 |
| 9 | 552 | 175 | 1.49 | 120 | 30 | 6.97 |
| 10 | 600 | 175 | 1.45 | 120 | 32 | 7.51 |
| 11 | 672 | 180 | 1.51 | 120 | 26 | 8.41 |
| 12 | 696 | 180 | 1.45 | 120 | 28 | 8.69 |
| 13 | 720 | 180 | 1.38 | 120 | 33 | 8.94 |
| 14 | 744 | 180 | 1.38 | 120 | 38 | 9.18 |
| 15 | 768 | 185 | 1.43 | 120 | 18 | 9.49 |
| 16 | 840 | 185 | 1.38 | 120 | 28 | 10.30 |

TABLE 10

CARBON NUMBER DISTRIBUTIONS FOR HEXENE FEED AND PRODUCTS

| CARBON NUMBER | FEED | RUN 4-4 | RUN 4-6 | RUN 4-10 | RUN 4-12 | RUN 4-14 | RUN 4-16 |
|---|---|---|---|---|---|---|---|
| wt % ≤ $C_5$ | 0.12 | 0.1 | — | — | — | — | — |
| $C_6$ | 84.0 | 86.4 | 87.4 | 88.1 | 87.5 | 87.8 | 87.7 |
| $C_7$ | 15.2 | 12.8 | 12.2 | 11.7 | 12.1 | 11.8 | 11.8 |
| $C_8$ | — | — | — | — | — | — | — |
| $C_9$ | — | 0.1 | — | — | — | — | — |
| $C_{10}$ | 0.14 | 0.1 | 0.1 | — | — | — | — |
| $C_{11}$ | 0.18 | 0.1 | 0.1 | — | — | — | 0.1 |
| $C_{12}$ | 0.37 | 0.3 | 0.2 | 0.2 | 0. | 0.3 | 0.3 |
| $C_{13}$ | 0.07 | — | — | — | — | — | — |
| $C_{14}$ | — | — | — | — | — | — | — |
| wt % paraffin | 9.85 | 9.80 | 9.88 | 9.77 | 9.72 | 9.73 | 9.76 |
| Temperature Reactor ° | — | 170 | 170 | 175 | 180 | 180 | 185 |
| VVH hr$^{-1}$ | — | 1.43 | 1.43 | 1.45 | 1.45 | 1.38 | 1.38 |
| wt % Sulphur on the Catalyst | — | 3.40 | 5.22 | 7.51 | 8.69 | 9.15 | 10.30 |

TABLE 11

ASTM DISTILLATION (D-1078) FOR HEXENE FEED AND PRODUCTS

| ASTM DISTILLATION RESULTS °C. | FEED | RUN 4-4 | 4-6 | 4-10 | 4-12 | 4-14 | 4-16 |
|---|---|---|---|---|---|---|---|
| IBP | 66.4 | 66.3 | 66.3 | 64.6 | 66.3 | 66.3 | 66.3 |
| 25% | 67.8 | 68.1 | 68.0 | 67.8 | 68.1 | 68.0 | 67.8 |
| 50% | 68.4 | 68.7 | 68.8 | 68.7 | 68.8 | 68.7 | 68.7 |
| 75% | 69.4 | 69.9 | 69.8 | 69.8 | 70.0 | 69.8 | 69.8 |
| 95% | 72.8 | 74.2 | 73.9 | 73.8 | 73.9 | 73.7 | 74.3 |
| DP | 73.8 | 75.2 | 75.0 | 75.2 | 75.1 | 75.5 | 75.2 |

As can be seen from Table 9, Runs 4-7, 4-11, and 4-15, the desulphurization level may be improved by small increases in operating temperature as the catalyst sulphur loading increases. In this Example, after the first 300 hours, total desulphurization was not attempted.

EXAMPLE 5

The procedure of Example 4 was repeated, but using spent Engelhard/Harshaw Ni-3288 catalyst, which had been used as a hydrogenation catalyst and which contained 1 wt % sulphur on start-up; the values given in Tables 12 and 13 show the increase in sulphur loading over this value. The results shown in Tables 12 to 14 indicate the effectiveness of this material in desulphurization.

TABLE 12

| RUN NUMBER 5- | TOTAL TIME ON STREAM hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 19 | 170 | 1.38 | 195 | 140 | 0.12 |
| 2 | 43 | 170 | 1.38 | 195 | 135 | 0.28 |
| 3 | 90.5 | 175 | 1.40 | 195 | 124 | 0.66 |
| 4 | 163 | 180 | 1.42 | 195 | 95 | 1.49 |
| 5 | 187 | 180 | 1.45 | 195 | 77 | 1.82 |
| 6 | 211 | 185 | 1.47 | 195 | 45 | 2.25 |
| 7 | 234 | 185 | 1.50 | 195 | 42 | 2.67 |

At start up, there is already 1% sulphur on catalyst.

TABLE 13

CARBON NUMBER DISTRIBUTIONS FOR HEXENE FEED AND PRODUCTS

| CARBON NUMBER | FEED | RUN 5-1 | 5-2 | 5-3 | 5-4 | 5-5 | 5-6 | 5-7 |
|---|---|---|---|---|---|---|---|---|
| wt % ≦ $C_5$ | 0.3 | 0.3 | 0.3 | 0.3 | 0.3 | 0.3 | 0.3 | 0.3 |
| $C_6$ | 87.4 | 88.4 | 88.7 | 88.2 | 88.5 | 89.2 | 88.3 | 87.9 |
| $C_7$ | 11.5 | 10.6 | 10.3 | 10.7 | 10.6 | 10.0 | 10.7 | 11.1 |
| $C_8$ | — | — | — | — | — | — | — | — |
| $C_9$ | — | — | — | — | — | — | — | — |
| $C_{10}$ | 0.1 | 0.1 | 0.1 | 0.1 | 0.1 | 0.1 | 0.1 | 0.1 |
| $C_{11}$ | 0.3 | 0.3 | 0.3 | 0.3 | 0.3 | 0.2 | 0.3 | 0.3 |
| $C_{12}$ | 0.3 | 0.2 | 0.2 | 0.2 | 0.2 | 0.2 | 0.2 | 0.3 |
| $C_{13}$ | 0.1 | 0.05 | 0.05 | 0.05 | 0.05 | 0.05 | 0.05 | 0.05 |
| $C_{14}$ | — | — | — | — | — | — | — | — |
| wt % paraffin | 21.6 | 17.7 | 17.2 | 17.8 | 17.2 | 17.4 | 17.3 | 17.2 |
| Temperature Reactor ° | — | 170 | 170 | 175 | 180 | 180 | 185 | 185 |
| VVH hr$^{-1}$ | — | 1.38 | 1.38 | 1.40 | 1.42 | 1.45 | 1.47 | 1.50 |
| Additional wt % Sulphur on the Catalyst | — | 0.12 | 0.28 | 0.66 | 1.49 | 1.82 | 2.25 | 2.67 |

TABLE 14

ASTM DISTILLATION (D-1078) FOR HEXENE FEED AND PRODUCTS

| ASTM DISTILLATION RESULTS °C. | FEED | RUN 5-3 | RUN 5-5 | RUN 5-7 |
|---|---|---|---|---|
| IBP | 64.7 | 64.7 | 64.7 | 64.6 |
| 25% | 67.6 | 66.4 | 66.4 | 66.5 |
| 50% | 67.1 | 67.3 | 67.3 | 67.2 |
| 75% | 68.4 | 68.6 | 68.5 | 68.5 |
| 95% | 72.5 | 73.4 | 72.8 | 72.4 |
| DP | 73.8 | 89.0 | 80.4 | 82.8 |

It will be noted from the results in Tables 10 and 13 that the hydrocarbon make-up of the feedstock was unaffected by desulphurization. It is believed that the low silicon content (less than 4%), high calcium content (more than 1%) and the low silicon:calcium ratio (less than 4:1) in the catalyst all contribute to this result.

EXAMPLE 6

Following the procedure of Example 1, fresh Engelhard/Harshaw Ni-3288 catalyst is charged to the reactor. Hexenes, heptenes, octenes and nonenes with various sulphur levels were used as feedstocks. After initial total desulphurization, sulphur breakthrough was allowed to occur in order to accelerate sulphur buildup on the catalyst. As the sulphur loading increased the operating temperature was raised in 5° C. increments from 165° C. to 185° C. By following this procedure an ultimate sulphur buildup of 12% on the catalyst was obtained.

Again following the procedure of Example 1, spent Engelhard/Harshaw Ni-3288 catalyst was loaded in the reactor. After treating the catalyst with various sulphur bearing olefin feeds and following the above mentioned operating procedure an ultimate sulphur buildup of 18% on the catalyst was obtained. Final operating temperatures of 195° C. were feasible without experiencing disadvantageous hydrocarbon product make-up.

This example illustrates the additional advantage of using spent catalyst rather than fresh, it being possible to treat a greater quantity of feedstock over the same quantity of catalyst.

EXAMPLE 7

The procedure of Example 2 was followed except that the catalyst was aminated by passing through it triethylamine at 1% concentration in a hexene feedstock for 24 hours at 170° C. and 29 bar (gauge) to maintain the feed in the liquid phase.

The results are shown in Tables 15 and 16 below, from which it can be seen that dimer formation has been prevented, with a similar sulphur removal performance.

TABLE 15

DESULPHURIZATION RESULTS, AMINE TREATED CATALYST

| RUN NUMBER 1- | TOTAL RUN TIME hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 1 | 24 | 170 | 1.70 | 180 | <1 | 0.36 |
| 2 | 45 | 175 | 1.61 | 180 | <1 | 0.67 |
| 3 | 69 | 180 | 1.65 | 180 | <1 | 1.02 |
| 4 | 93 | 185 | 1.69 | 180 | 1 | 1.38 |
| 5 | 164 | 185 | 1.63 | 180 | <1 | 2.40 |

TABLE 16

CARBON NUMBER DISTRIBUTIONS FOR HEXENE FEED AND PRODUCTS: AMINE TREATED CATALYST

| | | RUN | | | |
|---|---|---|---|---|---|
| CARBON NUMBER | FEED | 1-2 | 1-3 | 1-4 | 1-5 |
| wt % ≦ $C_5$ | 0.3 | 0.5 | 0.5 | 0.6 | 0.4 |
| $C_6$ | 87.4 | 86.2 | 86.3 | 86.2 | 86.4 |
| $C_7$ | 11.5 | 12.3 | 12.4 | 12.4 | 12.4 |
| $C_8$ | — | 0.1 | — | — | — |
| $C_9$ | — | — | — | — | — |
| $C_{10}$ | 0.1 | 0.1 | 0.1 | 0.1 | 0.1 |
| $C_{11}$ | 0.3 | 0.4 | 0.4 | 0.4 | 0.4 |
| $C_{12}$ | 0.3 | 0.3 | 0.2 | 0.2 | 0.2 |
| $C_{13}$ | 0.1 | 0.1 | 0.1 | 0.1 | 0.1 |
| $C_{14}$ | — | — | — | — | — |
| wt % paraffin | 21.6 | 21.7 | 21.2 | 21.5 | 21.3 |
| Delta $C_{12}$ + $C_{13}$ | — | 0 | 0 | 0 | 0 |
| Temperature Reactor °C. | — | 175 | 180 | 185 | 185 |
| VVH hr$^{-1}$ | — | 1.61 | 1.65 | 1.69 | 1.69 |
| wt % sulfur | — | 0.67 | 1.02 | 1.38 | 2.10 |

Note:
During Run 1-1 hexene with 1 wt % triethylamine was passed over the catalyst at 170° C.; following runs hexene only.

EXAMPLE 8

This example was carried out initially in substantially the same way as Example 2, but using fresh Engelhard-/Harshaw Ni-5126T 1/8 catalyst (analysis: Ni 59%; Si 6%; Al 5.1%; Ca 0.4%; Fe 0.1%) and using an olefin feed as set out in Table 18 below, with a paraffin content of 9.8%, chlorine 2 ppm, sulphur 120 ppm, S.G. (20/20° C.) 0.693, and maleic anhydride value 0.25 mg/g. Then, after 584 hours, when sulphur loading on the catalyst had reached 7.1% by weight, 1% by weight of triethylamine was incorporated in the hexene feed for 25 hours at 180° C. As can be seen from the results in Tables 17 and 18 below, the amination of the catalyst effectively prevented dimer formation.

TABLE 17

DESULPHURIZATION RESULTS

| RUN NUMBER 2- | TOTAL RUN TIME hrs | REACTOR TEMPERATURE °C. | VVH hr$^{-1}$ | SULPHUR IN ppm | SULPHUR OUT ppm | SULPHUR ON CAT. wt % |
|---|---|---|---|---|---|---|
| 6 | 274 | 170 | 1.53 | 120 | 1 | 3.45 |
| 8 | 394 | 170 | 1.55 | 120 | 6 | 4.90 |
| 13 | 584 | 180 | 1.57 | 120 | 7 | 7.13 |
| 14 | 609 | 180 | 1.54 | 120 | 12 | 7.41 |
| 15 | 632 | 180 | 1.61 | 120 | 10 | 7.68 |
| 16 | 656 | 180 | 1.58 | 120 | 10 | 7.96 |
| 17 | 679 | 180 | 1.58 | 120 | 11 | 8.22 |

Note:
Added 1 wt % triethylamine to hexene feed during run 14.

TABLE 18

CARBON NUMBER DISTRIBUTION HEXENE FEED AND PRODUCTS CATALYST AMINE TREATED DURING RUN 2-14

| | | RUN | | | | | |
|---|---|---|---|---|---|---|---|
| CARBON NUMBER | FEED | 2-6 | 2-8 | 2-13 | 2-15 | 2-16 | 2-17 |
| wt % = $C_5$ | 0.12 | — | — | — | — | — | — |
| $C_6$ | 84.0 | 85.6 | 84.9 | 83.5 | 86.9 | 87.1 | 87.5 |
| $C_7$ | 15.2 | 13. | 13.8 | 14.1 | 12.7 | 12.5 | 12.1 |
| $C_8$ | — | — | — | — | — | — | — |
| $C_9$ | — | — | — | — | — | — | — |
| $C_{10}$ | 0.14 | 0.3 | 0.1 | 0.1 | 0.1 | 0.1 | 0.1 |
| $C_{11}$ | 0.18 | 0.1 | 0.1 | 0.1 | 0.1 | 0.1 | 0.1 |
| $C_{12}$ | 0.37 | 0.9 | 1.0 | 2.2 | 0.3 | 0.2 | 0.2 |
| $C_{13}$ | 0.07 | — | — | 0.1 | — | — | — |
| $C_{14}$ | — | — | — | — | — | — | — |
| wt % paraffin | 9.85 | 9.87 | 9.76 | 10.01 | 9.67 | 9.42 | 9.53 |
| Delta $C_{12}$ + $C_{13}$ wt % | — | 0.5 | 0.6 | 1.9 | 0 | 0 | 0 |
| Temperature Reactor °C. | — | 170 | 170 | 180 | 180 | 180 | 180 |
| VVH hr$^{-1}$ | — | 1.53 | 1.55 | 1.57 | 1.61 | 1.58 | 1.58 |
| wt % sulphur on the catalyst | 3.45 | 4.90 | 4.90 | 7.13 | 7.68 | 7.96 | 8.22 |

Note:
During Run 2-14 for 25 hours hexene with 1 wt % triethylamine was passed over the catalyst at 180° C. Following runs hexene only.

Examples 7 to 8 show the improvements that can be realised by using an aminated nickel-containing catalyst.

Since it is believed that the use of aminated nickel-containing feedstocks is new this is yet a further feature of the present invention.

We claim:

1. A process for desulphurising an olefin-containing hydroformylation feedstock prior to hydroformylation of the olefin-containing feedstock wherein a sulphur-bearing olefin-containing feedstock is contacted under substantially non-hydrogenating conditions in the absence of hydrogen with a nickel-containing catalyst, whereby the sulphur content of the feedstock is lowered, the temperature and pressure being such that the feedstock is liquid, the temperature being 150° C. to 400° C. and the pressure being 20–40 bar, the catalyst containing at least 35% by weight up to 65 wt. % nickel.

2. A process as claimed in claim 1, wherein the olefin is a $C_3$ to $C_{18}$, preferably a $C_4$ to $C_6$, olefin.

3. A process as claimed in claim 1, wherein the olefin is hexene.

4. A process as claimed in claim 1, wherein the nickel-containing catalyst is supported on a refractory material, advantageously a silica/alumina support.

5. A process as claimed in claim 1, wherein the nickel-containing catalyst is a spent hydrogenation catalyst.

6. A process according to claim 1 or claim 5 in which the nickel-containing catalyst is aminated.

7. The process as claimed in any one of claims 1 to 5, wherein the catalyst is on a support containing silicon and the silicon content is less than 4%, or wherein the catalyst is on a support containing calcium and the calcium content is at least 1%, based on the total weight of catalyst and support.

8. The process as claimed in any one of claims 1 to 5, wherein the catalyst is on a support containing silicon and calcium, and the weight ratio of silicon:calcium is less than 4:1.

* * * * *